US008510053B2

(12) United States Patent
Nishio et al.

(10) Patent No.: US 8,510,053 B2
(45) Date of Patent: Aug. 13, 2013

(54) METHOD FOR MODIFYING A PROPERTY OF A PROTEIN

(75) Inventors: Yosuke Nishio, Kawasaki (JP); Eiichiro Kimura, Tokyo (JP); Yoshihiro Usuda, Kawasaki (JP); Kazuho Ikeo, Mishima (JP); Yoji Nakamura, Mishima (JP); Takashi Gojobori, Mishima (JP); Yutaka Kawarabayashi, Kisarazu (JP); Yumi Hino, Yokohama (JP); Eiichi Hori, Tokyo (JP); Jun Yamazaki, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 1583 days.

(21) Appl. No.: 10/933,280

(22) Filed: Sep. 3, 2004

(65) Prior Publication Data

US 2005/0233308 A1    Oct. 20, 2005

Related U.S. Application Data

(63) Continuation of application No. PCT/JP03/02495, filed on Mar. 4, 2003.

(30) Foreign Application Priority Data

Mar. 4, 2002    (JP) .................................. 2002-57863

(51) Int. Cl.
*G01N 33/50*    (2006.01)

(52) U.S. Cl.
USPC ........................................................... 702/19

(58) Field of Classification Search
None
See application file for complete search history.

(56) References Cited

U.S. PATENT DOCUMENTS

| | | | | |
|---|---|---|---|---|
| 2009/0636458 | * | 8/2000 | Matsuzaki et al. | 435/6 |
| 2009/0868338 | * | 6/2001 | Kanno et al. | 435/6 |
| 2002/0137094 | A1 | 9/2002 | Yamagishi | 435/7.1 |
| 2002/0155556 | A1 | 10/2002 | Imaizumi et al. | 435/115 |
| 2003/0232338 | A1 | 12/2003 | Usuda et al. | 435/6 |
| 2004/0170985 | A1 | 9/2004 | Usuda et al. | 435/6 |
| 2004/0170986 | A1 | 9/2004 | Usuda et al. | 435/6 |
| 2004/0170987 | A1 | 9/2004 | Usuda et al. | 435/6 |
| 2004/0197918 | A1 | 10/2004 | Matsuzaki et al. | 435/471 |
| 2004/0229305 | A1 | 11/2004 | Usuda et al. | 435/69.1 |

FOREIGN PATENT DOCUMENTS

| | | |
|---|---|---|
| EP | 1 182 253 | 2/2002 |
| WO | WO 01/47956 | 7/2001 |
| WO | PCT/JP03/002495 | 6/2003 |
| WO | PCT/JP03/002495 | 12/2003 |

OTHER PUBLICATIONS

Gianese, G. et al., "Structural adaptation of enzymes to low temperatures", Protein Engineering, vol. 14, No. 3, 141-148 (2001).
McDonald, J., "Patterns of Temperature Adaptation in Proteins from the Bacteria *Deinococcus radiodurans* and *Thermus thermophilus*", Mol. Biol. Evol., vol. 18, No. 5, 741-749 (2001).
McDonald, J. et al., "Patterns of Temperature Adaptation in Proteins from *Methanococcus* and *Bacillus*", Mol. Biol. Evol., vol. 16, No. 12, 1785-1790 (1999).
Vieille, C., et al., "Hyperthermophilic Enzymes: Sources, Uses, and Molecular Mechanisms for Thermostability", Microbiology and Molecular Biology Reviews, Mar. 2001, vol. 65, No. 1, p. 1-43.
Haney, P. J., et al., "Thermal adaptation analyzed by comparison of protein sequences from mesophilic and extremely thermophilic *Methanococcus* species", Proc. Natl. Acad. Sci. USA, Mar. 1999, vol. 96, pp. 3578-3583.
European Search Report Feb. 1, 2005
Kawarabayashi, Y., et al., "Complete Genome Sequence of an Aerobic Thermoacidophilic Crenarchaeon, *Sulfolobus tokodaii* strain7," DNA Res. 2001;8:123-140.
Notice of Reason for Rejection from Japanese Patent App. No. 2002-057863 (Nov. 20, 2007) with partial English translation.

* cited by examiner

*Primary Examiner* — Jason Sims

(74) *Attorney, Agent, or Firm* — Shelly Guest Cermak; Cermak Nakajima LLP

(57)    ABSTRACT

The present invention relates to a method for modifying a property of a protein. The present invention also relates to a method for producing a protein which has a modified property, and a method for producing a microorganism which has a modified property. The present invention is useful in the field of microbial industrial production and the like.

9 Claims, No Drawings

US 8,510,053 B2

METHOD FOR MODIFYING A PROPERTY OF A PROTEIN

This application is a continuation of application PCT/JP03/02495, filed Mar. 4, 2003.

BACKGROUND OF THE INVENTION

1. Field of the Invention

The present invention relates to a method for modifying a property of a protein. The present invention also relates to a method for producing a protein which has a modified property, and a method for producing a microorganism which has a modified property. The present invention is useful in the field of microbial industrial production and the like.

2. Brief Description of the Related Art

Proteins and microorganisms which have an activity in an environment which is different from that in environments preferred by usual microorganisms may have advantages over other proteins and microorganisms. For example, proteins which are active at a high temperature, in particular, thermostable enzymes, are advantageous over those that are inactivated at high temperatures because they do not need to be cooled to be active. Usually, such thermostable proteins are often produced by bacteria known as thermophilic bacteria, which can grow at a high temperature. Accordingly, when a thermostable protein is designed, amino acid sequences of corresponding proteins within a group of such thermophilic bacteria are analyzed, and commonly observed characteristics in the amino acid sequences are used for reference in many cases. Alternatively, techniques for analyzing three-dimensional structures of proteins produced by thermophilic bacteria, estimating a structure which imparts thermostability based on this information, and modifying the structure of a non-thermostable protein so as to have such a structure, and the like, are employed. Furthermore, a method has been proposed in which amino acid sequences of evolutionarily corresponding proteins derived from two or more species in an evolutionary tree are compared, and an amino acid sequence of a proper ancestral protein estimated to be a protein of a hyperthermophilic bacterium is estimated to improve the thermostability.

SUMMARY OF THE INVENTION

Objects of the present invention are to provide a method for modifying a property of a protein, for example, thermostability, a method for producing a protein having said modified property, and a method for producing a microorganism having said modified property.

More specifically, it is an object of the present invention to provide a method for modifying a property of a protein, comprising (a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under at least one optimum growth condition when compared with the first microorganism, (b) comparing an amino acid sequence encoded by a gene from the first microorganism to an amino acid sequence encoded by the orthologous gene from the second microorganism, (c) detecting substitutions between the amino acid sequence encoded by a gene from the first microorganism and the amino acid sequence encoded by a gene from the second microorganism for each pair of orthologous genes, (d) compiling the detected amino acid substitutions for each amino acid substitution type, (e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism, (f) identifying and labelling the amino acid substitutions which occur at a high frequency as amino acid substitutions which are involved in said optimum growth condition, and (g) introducing one or more of the amino acid substitutions identified in (f) into the gene encoding the protein to modify a property of the protein.

It is a further object of the present invention to provide the method as described above, wherein said optimum growth condition is optimum growth temperature, and the property of the protein is thermostability.

It is a further object of the present invention to provide the method as described above, wherein genes having an identity of 60% or more and less than 95% on the amino acid sequence level are selected as genes which are orthologs to each other.

It is a further object of the present invention to provide the method as described above, wherein the first microorganism and the second microorganism are coryneform bacteria.

It is a further object of the present invention to provide the method as described above, wherein the first microorganism is *Corynebacterium glutamicum*, and the second microorganism is *Corynebacterium efficiens*.

It is an object of the present invention to provide a method for improving thermostability of a protein, comprising introducing into said protein two or more amino acid substitutions selected from the group consisting of:

(i) substitution of an arginine residue for a lysine residue,
(ii) substitution of a threonine residue for a serine residue, and
(iii) substitution of an alanine residue for a serine residue.

It is an object of the present invention to provide a method for producing a protein having a modified property comprising:

(a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under at least one optimum growth condition when compared with the first microorganism, (b) comparing an amino acid sequence encoded by a gene from the first microorganism to an amino acid sequence encoded by the orthologous gene from the second microorganism, (c) detecting substitutions between the amino acid sequence encoded by a gene from the first microorganism and the amino acid sequence encoded by a gene from the second microorganism for each pair of orthologous genes, (d) compiling the detected amino acid substitutions for each amino acid substitution type, (e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism, (f) identifying and labelling the amino acid substitutions which occur at a high frequency as amino acid substitutions which are involved in said optimum growth condition, and (g) introducing one or more of the amino acid substitutions identified in (f) into the gene encoding the protein to modify a property of the protein, (h) introducing said gene obtained in (g) into a suitable host for gene expression to express the protein having a modified property.

It is a further object of the present invention to provide the method as described above, further comprising the steps of:

(i) testing the property of the protein obtained in (h), and (j) selecting a protein having an improved property relating to said optimum growth condition.

It is a further object of the present invention to provide the method as described above, wherein said optimum growth condition is optimum growth temperature, and the property of the protein is thermostability.

It is a further object of the present invention to provide a method for producing a microorganism having a modified property comprising:

(a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under at least one optimum growth condition when compared with the first microorganism, (b) comparing an amino acid sequence encoded by a gene from the first microorganism to an amino acid sequence encoded by the orthologous gene from the second microorganism, (c) detecting substitutions between the amino acid sequence encoded by a gene from the first microorganism and the amino acid sequence encoded by a gene from the second microorganism for each pair of orthologous genes, (d) compiling the detected amino acid substitutions for each amino acid substitution type, (e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism, (f) identifying and labelling the amino acid substitutions which occur at a high frequency as amino acid substitutions which are involved in said optimum growth condition, and (g) introducing one or more of the amino acid substitutions identified in (f) into a chromosomal DNA of a microorganism to modify a property of said microorganism.

It is a further object of the present invention to provide the method as described above, wherein said optimum growth condition is optimum growth temperature, and the property of the protein is thermostability.

DESCRIPTION OF THE PREFERRED EMBODIMENTS

The inventors of the present invention assiduously studied in order to achieve the above objects. As a result, they found that by using the genome sequences of closely related microorganisms which show a difference in a certain property and comparing the primary structure information of a large number of proteins, amino acid substitutions contributing to the identified property could be determined. Then, they took note of thermostability as a property of a protein. They concluded that amino acid substitutions contributing to thermostabilization could be predicted by comparing moderately thermophilic bacteria growing at about 55 to 74° C. or bacteria which show an even lower optimum growth temperature, but not hyperthermophilic bacteria which grow at about 75° C. or higher, with closely related bacteria with a clearly lower optimum growth temperature. Furthermore, they confirmed that the amino acid substitutions which might be involved in temperature resistance could be precisely predicted by comparing a large number of amino acid sequences of orthologous genes extracted from the genome sequences of two types of closely related bacteria showing different optimum growth temperatures, that is, bacteria of a thermophilic type and a mesophilic type, and thus accomplished the present invention.

The method for modifying a property of a protein of the present invention comprises the following steps of:

(a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism and but grows under at least one different optimum condition, when compared with the first microorganism, (b) comparing an amino acid sequence encoded by a gene from the first microorganism to an amino acid sequence encoded by the orthologous gene from the second microorganism, (c) detecting substitutions between the amino acid sequence encoded by a gene from the first microorganism and the amino acid sequence encoded by a gene from the second microorganism for each pair of orthologous genes and (d) compiling the detected amino acid substitutions for each amino acid substitution type, (e) calculating a frequency of each amino acid substitution type, wherein for each detected amino acid substitution type, a correction is make by subtracting the total number of substitution types which occur from the first microorganism to the second microorganism from the total number of the same substitution type which occurs in the reverse direction, or from the second microorganism to the first microorganism, (f) identifying and labelling the amino acid substitutions which occur at a higher frequency as amino acid substitutions which are involved in said optimum growth condition, (g) introducing one or more of the amino acid substitutions identified in (f) into the gene encoding the protein to modify a property of the protein.

In the present invention, the optimum growth condition or optimum conditions for growth means a condition suitable for survival or growth of a microorganism, and examples thereof include optimum growth temperature, optimum growth pH, optimum growth osmotic pressure and so forth. Properties of proteins to be modified by the present invention which correspond to these optimum growth conditions, and examples thereof include thermostability, acid or alkali resistance, halophilism and so forth. The degree of difference between the two chosen microorganims in their optimum growth condition is not particularly limited so long as those of the first microorganism and the second microorganism are different. However, for example, when the condition is growth temperature, the optimum growth temperatures are preferably different by 5° C. or more.

In the present invention, the two types of closely related microorganisms having a difference in at least one their optimum growth conditions are used as information sources of amino acid substitutions that can impart a desired property to a protein. Examples of the second microorganism closely relating to the first microorganism include microorganisms that have taxonomic properties similar to those of the first microorganism or are at a close evolutionary distance from the first microorganism in view of molecular phylogeny. More specifically, the examples include microorganisms belonging to the same genus or bacterial strains belonging to the same species. Furthermore, specifically, the examples include microorganisms containing 1000 or more orthologs having a homology in such a degree that amino acid substitutions between two types of genes can be extracted, preferably an identity of 60% or more.

Although microorganisms to which the present invention can be applied are not particularly limited, they are desirably industrially useful microorganisms. Examples thereof include, for example, Gram-negative bacteria of the genus *Escherichia, Serratia* or the like, and Gram-positive bacteria of the genus *Corynebacterium, Brevibacterium, Bacillus* or the like.

Examples of the closely relating microorganisms which show a difference in at least one optimum growth condition include, for example, *Corynebacterium glutamicum* and *Corynebacterium efficiens* as microorganisms, and which have different optimum growth temperatures. *Corynebacterium glutamicum* is a mesophilic bacterium whereby the optimum growth temperature is 25 to 35° C. Its genome sequence is open to public in the DNA Data Bank Japan (DDBJ), GenBank, EMBL and so forth (accession numbers AX120085, AX127144, AX127145, AX127146, AX127147, AX127148, AX127149, AX127150, AX127151, AX127152 and AX127153). Furthermore, *Corynebacterium efficiens* is a moderately thermophilic bacterium isolated as *Corynebacterium thermoaminogenes* whereby the optimum growth temperature is 35 to 45° C. (Japanese Patent Laid-open (Kokai) No. 63-240779, Japanese Patent Publication (Kokoku) No. 7-63383). However, it has been proposed to be re-classified as *Corynebacterium efficiens* (Fudou R. et. al., Int. J. Syst. Evol. Microbiol., 52:1127-1131, 2002). The term *Corynebacterium efficiens* used in the present specification refers to a bacterium previously classified as *Corynebacterium thermoaminogenes*. Specific examples of bacterial strains classified as *Corynebacterium efficiens* include the *Corynebacterium efficiens* AJ12340 strain (also referred to as YS-40 strain), AJ12308 strain (also referred to as YS-52 strain), AJ12309 strain (also referred to as YS-155 strain), AJ12310 strain (also referred to as YS-314 strain) and so forth.

The AJ12340 strain was originally deposited at the Fermentation Research Institute, Agency of Industrial Science and Technology, Ministry of International Trade and Industry (currently the independent administrative institution, International Patent Organism Depository, National Institute of Advanced Industrial Science and Technology, Tsukuba Central 6, 1-1, Higashi 1-Chome, Tsukuba-shi, Ibaraki-ken, 305-8566, Japan) on Mar. 13, 1987 and received an accession number of FERM P-9277. Then, the deposit was converted to an international deposit under the provisions of the Budapest Treaty on Oct. 27, 1987, and received an accession number of FERM BP-1539. Furthermore, the AJ12308, AJ12309 and AJ12310 strains were originally deposited at the aforementioned depository on Mar. 10, 1987 and received accession numbers of FERM P-9244, FERM P-9245 and FERM P-9246, respectively. Then, the deposits were converted to international deposits under the provisions of the Budapest Treaty on Oct. 27, 1987, and received accession numbers of FERM BP-1540, FERM BP-1541 and FERM BP-1542, respectively.

Genes which are orthologs to each other are extracted from the aforementioned two types of closely relating microorganisms. The term "gene" used in the present specification means a region in a genome sequence, which encodes or is predicted to encode a protein. The term "orthologs" means genes derived from different microorganisms' genomes which have high homology with each other.

As genome sequences of microorganisms used in the present invention, already published sequences or newly determined sequences may be used. For example, genome sequences of a large number of microorganisms have been published since that of *Haemophilus influenzae* was published (Fleischman R. D. et. al., Science, 269:496-512, 1995) and can be utilized. Genome sequences of microorganisms whose sequences have not been published can be determined by methods represented by the whole genome shotgun approach described in the aforementioned report of Fleischman et al.

Genes which are orthologs to each other are selected as follows, for example. First, sequences predicted to encode proteins are extracted from the genome sequence of each microorganism. Then, each gene sequence is translated into an amino acid sequence and the homology is calculated.

Programs for predicting genes estimated to encode proteins from a genome sequence of a microorganism include those utilizing the Hidden Markov model. Such programs are frequently used and major examples include Glimmer (Delcher, A. L. et. al., Nucleic Acids Res., 27:4636-4641, 1999), GeneHacker (Yada, T. and Hirosawa, M., DNA Res., 3:336-361, 1996; Yada, T. et. al., Proc. Fifth Int. Conf. Intell. Syst. Mol. Biol., pp. 354-357, 1997), GeneMark.hmm (Lukashin, A. and Borodovsky M., Nucleic Acids Res., 26:1107-1115, 1998; Besemer, J. and Borodovsky M., Nucleic Acids Res., 27:3911-3920, 1997) and so forth.

Genes extracted from the genome sequences of two species can be translated into amino acid sequences, and the calculated homologies used to detect orthologs as ORFs having the highest homology with each other (Snel, B., Bork, P. and Huynen, M. A., Nat. Genet., 21:108-110, 1999; Tatusov, R. L., Koonin, E. V. and Lipman, D. J., Science, 278:631-637, 1997; Tejaua, F., Lazcano, A. and Dujon, B., Genome Res., 9:550-557, 1999). To examine orthologs, commonly used homology search methods such as FASTA (Lipman, D. J. and Pearson, W. R., Science, 227:1435-1441, 1985) and Smith-Waterman (Smith, T. F. and Waterman, M. S., J. Mol. Biol., 147:195-197, 1981) are available. The most commonly used method is BLASTP (Altschul, F. S., Maddenm T. L., Schaffer, A. A., Zhang, J., Zhang, Z., Miller, W. and Lipman, D. J., Nucleic Acids Res., 25:3389-3402, 1997).

To compare two amino acid sequences, alignment of the amino acid sequences is performed in which the sequences are aligned in consideration of properties of amino acids. As an alignment technique, CLUSTAL W (Thompson, J. D., Higgins, D. G and Gibson, T. J., Nucleic Acids Res., 22:4673-4680, 1994) is well known. However, to align two sequences by comparing them from the N-terminus, a technique called pairwise alignment is effective, and software programs therefor such as needle (Needleman, S. B. and Wunsch, C. D., J. Mol. Biol., 48:443-453, 1970), matcher (Huang, X. and Miller, W., Adv. Appl. Math., 12:373-381, 1991) and stretcher (Myers, E. and Miller, W., CABIOS, 4:11-17, 1988) are available. The stretcher is a software program for performing alignment on the basis of a principle called global alignment, which outputs overall similarities between two sequences having almost the same lengths as a result, and is suitable for the purpose of the present study.

In the present invention, it is preferable to select 1000 or more genes from each microorganism, resulting in pairs of genes which are orthologs to each other, preferably 1500 or more pairs, more preferably 2000 or more pairs. Furthermore, the p-distance (Nei M. et al., Molecular Evolution and Phylogenetics, pp. 17-31, Oxford University Press, New York, 2000) between the orthologous genes is preferably 0.3 or less. If the distance is larger than this value, it becomes more likely that parallel or backward substitutions would be extracted as amino acid substitutions. Furthermore, genes which are orthologs to each other preferably have an identity of 60% or more and less than 95% on the amino acid sequence level. If identity is lower than this range, it becomes difficult to perform the alignment, and it becomes more likely that amino acids will not correspond to each other one-to-one. Genes having an identity higher than this range do not necessarily need to be excluded. However, since such genes typically encode proteins with extremely conserved functions, it is highly likely that they do not affect phenotypes.

For each pair of orthologous genes selected as described above, amino acid substitutions between an amino acid sequence encoded by a gene of the first microorganism and an amino acid sequence encoded by a gene of the second microorganism are detected. Amino acid substitutions present between two genes can be detected as a result of the aforementioned gene alignment. On the basis of the results, the detected amino acid substitutions are compiled and the frequency of each type of amino acid substitution can be calculated. Subsequently, for each detected amino acid substitution type, a correction is made by subtracting the total number of substitution types which occur from the first microorganism to the second microorganism from the total number of the same substitution type which occur in the reverse direction, or from the second microorganism to the first microorganism, That is, from a number of particular substitutions (for example, substitution of lysine in the second microorganism gene for arginine in the first microorganism gene), the number of substitutions in the reverse direction to the particular substitution (substitution of arginine in the second microorganism gene for lysine in the first microorganism gene) is subtracted. Specifically, this is performed as follows, for example.

On the assumption that amino acids substitutions occur as a one-to-one amino acid correspondence, the alignment results are compiled as a matrix of 20 rows and 20 columns comprising the number of amino acid substitutions for all the 20 types of amino acids. This is assumed as a mathematical matrix (hereinafter, referred to as "A"), and a transposed matrix is created to simultaneously evaluate the reverse amino acid substitutions (hereinafter, referred to as "$A^{-1}$"). Then, (matrix A—transposed matrix $A^{-1}$)/2 is calculated (hereinafter, this calculation result will be referred to as "substitution evaluation index").

Among the amino acid substitutions extracted as described above, amino acid substitutions occurring at a higher substitution frequency (having a higher substitution evaluation index) are identified as the amino acid substitutions involved in the optimum growth condition of the second microorganism. The number of amino acid substitutions to be identified is not particularly limited, and is preferably 2 to 10 types, more preferably 2 to 5 types, particularly preferably 2 to 3 types. It is generally known that isoleucine, valine, leucine and methionine are amino acids that are likely to cause mutation among them (Kreil, D. P. et al., Nucleic Acids Res., 29:1608-1615, 2001). Therefore, among amino acid substitutions occurring at a higher substitution frequency, it is preferable to select substitutions occurring at a higher frequency than those of substitutions among isoleucine, valine, leucine and methionine.

As described above, the following amino acid substitutions, for example, are identified as amino acid substitutions involved in the impartation of thermostability of *Corynebacterium efficiens* to *Corynebacterium glutamicum*:
(i) Substitution of an arginine residue for a lysine residue
(ii) Substitution of a threonine residue for a serine residue
(iii) Substitution of an alanine residue for a serine residue.

One or more amino acid substitutions identified as described above are introduced into a protein whereby said property is to be modified. The objective protein to have the modified property imparted is not particularly limited, and examples thereof include, for example, proteins that preferably function under an optimum growth condition particular to the aforementioned second microorganism. Such proteins may be proteins of the aforementioned first microorganism or proteins of other microorganisms so long as they are proteins of microorganisms having a different optimum growth condition compared with that of the second microorganism. One type of amino acid substitution may be introduced at one site or two or more sites.

To introduce an amino acid substitution into an objective protein, a mutation can usually be introduced into a gene encoding the aforementioned protein by a technique utilized in the protein engineering art, such as site-directed mutagenesis, so that a desired amino acid substitution occurs. Furthermore, such a protein can also be produced by introducing the gene which has a mutation into a host suitable for gene expression utilizing a technique used in protein production based on a gene recombination technique to express a mutant protein having a modified property. As for the produced mutant proteins, the aforementioned property is tested, if necessary, to select a protein of which property has been modified as intended.

Furthermore, a microorganism having a modified property such as thermostability can be obtained by introducing the identified amino acid substitution into a gene on a chromosome of a target microorganism. The amino acid substitution can be introduced into the gene on a chromosome by, for example, preparing a gene introduced with a target mutation or a fragment thereof beforehand and substituting the mutant gene for the gene on chromosome on the basis of a gene substitution technique utilizing homologous recombination.

As methods for isolation of gene, digestion and ligation of DNA, transformation and so forth required for the aforementioned procedures, usual methods known to those skilled in the art can be used. Such methods are described in Sambrook, J., Fritsch, E. F. and Maniatis, T. "Molecular Cloning A Laboratory Manual, Second Edition", Cold Spring Harbor Laboratory Press (1989) and so forth.

To obtain a microorganism having a modified property, an amino acid substitution that can impart a desired property can be introduced into a gene encoding a protein so that a property of one or more proteins of the microorganism is modified.

As described above, a protein and microorganism having a modified property can be obtained. Specifically, for example, a protein such as an enzyme that functions at a higher temperature as compared with a wild-type protein or a microorganism having an optimum growth temperature raised can be obtained. Increase of culture temperature is considered to be an important technical factor for improving the economy of the industrial production of amino acids by fermentation, in addition to improvement of yield per saccharide, reduction of culture time, improvement of accumulated amino acid concentrations and so forth. That is, the culture is usually performed at an optimum fermentation temperature, and the optimum temperature of *Corynebacterium glutamicum* is 31.5° C. Since heat is generated by fermentation when the culture is started, the temperature in the culture increases, and amino acid production markedly decreases. Therefore, a cooling unit is necessary to maintain the culture broth at optimum temperature. On the other hand, if the culture temperature can be elevated, the energy necessary for cooling can be reduced, and furthermore, the cooling power of the unit can be reduced. Therefore, if a bacterial strain having improved thermostability can be produced by imparting thermostability comparable with that of *Corynebacterium efficiens* to a protein exhibiting low thermostability in a bacterial strain having improved amino acid productivity such as *Corynebacterium glutamicum* and further allowing to the bacterial strain to have such a thermostabilized protein, industrial usefulness of the strain will be clearly increased. For example, if a thermostable enzyme or bacterial strain is used, the load of temperature control during the reaction is relieved, the reaction can be performed at a high temperature, and therefore, the reaction rate becomes higher. Furthermore, since the reaction can be performed at a high temperature, contamination of other microorganisms can be minimized.

Furthermore, the method of the present invention can be used to produce a protein or microorganism suitable for a certain type of growth condition other than culture temperature.

BEST MODE FOR CARRYING OUT THE INVENTION

Hereafter, the present invention will be explained more specifically by way of the following non-limiting examples.

EXAMPLE 1

Determination of the Genome Sequence of *Corynebacterium efficiens*

Preparation of the Genomic DNA and Preparation of Shotgun Clones

A genomic DNA was extracted from the *Corynebacterium efficiens* AJ12340 strain by using Bacterial Genome DNA Purification Kit (Advanced Genetic Technologies). The following procedure is described in detail in the reference of Kawarabayashi et al. (Kawarabayashi, Y., et. al., DNA Res., 8:123-140, 2001). The genomic DNA of *Corynebacterium efficiens* was ultrasonicated in three stages of 5, 10 and 20 seconds by using an ultrasonicator, Biorupter (Cosmo Bio), at an output of L. The resultant solution was subjected to electrophoresis using an agarose gel, and DNA fragments having sizes of 0.8 to 1.2 kb and 2.0 to 2.5 kb were excised and cloned into the HincII site of pUC 118. As described above, a shotgun library consisting of short (0.8 to 1.2 kb) and long fragments (2.0 to 2.5 kb) was prepared.

(2) Sequencing of Shotgun Library

Plasmid DNAs in the aforementioned shotgun library comprising short (0.8 to 1.2 kb) and long fragments (2.0 to 2.5 kb) were prepared by using automatic DNA isolators P1-100 and P1-200 (Kurabo Industries Ltd.). The sequencing reaction was performed by using these plasmid DNAs as templates and ABI PRISM BigDye Terminator Cycle Sequencing Ready Reaction Kit (PERKIN ELMER) or ABI PRISM BigDye Primer Cycle Sequencing Ready Reaction Kit (PERKIN ELMER). For the short fragment library, each sequence at one end was determined by using M13 forward primer (−21 M13) as a primer. For the long fragment library, sequences at the both ends were determined by using M13 forward primer (−21 M13) and M13 reverse primer (M13 Reverse). PCR System 9600 (PERKIN ELMER) or DNA Engine PTC-200 (MJ RESEARCH) was used for the reaction. The nucleotide sequences of the sequencing reaction products were analyzed by using ABI PRISM 377 DNA Sequencer.

(3) Assembling and Sequencing of Gap Region

Raw data about 70,000 sequences were assembled by using an assembling software program, Phred-Phrap (CodonCode), and the raw data contained in the obtained contigs were assembled again using Sequencer (Gene Codes) to confirm and correct the nucleotide sequences. The nucleotide sequences of the gap portions between the contigs were determined by walking the shotgun clones including a long fragment using synthetic primers. Thus, the entire 3.14 million base pair genome sequence of *Corynebacterium efficiens* was determined. This genome sequence was given accession numbers of BA000035 or AP005214 to AP005224 from the DNA Data Bank of Japan (DDBJ), and was registered and opened to public.

EXAMPLE 2

Extraction of Amino Acid Substitutions by Comparison of Genome Sequences of *Corynebacterium glutamicum* and *Corynebacterium efficiens*

Sequence Information of *Corynebacterium glutamicum*

As the genome sequence of the mesophilic bacterium, *Corynebacterium glutamicum*, the nucleotide sequences of the *Corynebacterium glutamicum* ATCC 13032 strain registered with accession numbers of AX120085, AX127144, AX127145, AX127146, AX127147, AX127148, AX127149, AX127150, AX127151, AX127152 and AX127153 at the DNA Data Bank Japan were used.

(2) Prediction of Genes Encoding Proteins

Genes encoding proteins were predicted by using a gene identification software program, Glimmer, based on the principle of Hidden Markov models (Delcher, A. L. et al., Nucleic Acids Res., 27:4636-4641, 1999). Models used for the gene prediction were created on the basis of the genome sequences of *Corynebacterium glutamicum* and *Corynebacterium efficiens* according to the manual of Glimmer. Furthermore, the Shine-Dalgarno sequence (hereinafter, referred to as "SD sequence") was used to enhance precision of the gene prediction by execution of Glimmer. The SD sequence is a sequence for binding of mRNA to 16S RNA on a ribosome, which is a translation apparatus, at the time of translation of a gene. The used SD sequence was a sequence (5'-AGAAAGAGG-3') complementary to the sequence at the 3' end of 16S rRNA of *Corynebacterium glutamicum* (Amador, J. M. E. et al., Microbiology, 145:915-924, 1999).

(3) Extraction of Orthologs of *Corynebacterium glutamicum* and *Corynebacterium efficiens*

Pairs of genes that had the highest homology with each other among the extracted genes encoding proteins were assumed as orthologs (Snel, B. et al., Science, 278:631-637, 1997; Tejaua, F. et al., Genome Res., 9:550-557, 1999). Specifically, the nucleotide sequences of the genes encoding proteins were translated into amino acid sequences, and pairs of genes that showed the highest score for each other as a result of execution of BLASTP (Altschul, F. S. et al., Nucleic Acids Res., 25:3389-3402, 1997), which is the most commonly used for homology search, were selected as orthologs. BLASTP was executed under the default conditions using BLOSUM62, which is commonly used as a matrix. 2178 genes were extracted and identified as orthologs between the genomes of *Corynebacterium glutamicum* and *Corynebacterium efficiens*.

(4) Extraction of Amino Acid Substitutions between Orthologs

To compare the orthologs, pairwise alignment was performed, in which the gene sequences of *Corynebacterium glutamicum* and *Corynebacterium efficiens* were aligned from the N-terminus in consideration of properties of amino acids. A software program called stretcher was used for the pairwise alignment. The stretcher establishes alignment on the basis of the principle called global alignment, which outputs overall similarities between two sequences having almost the same lengths as a result (Myers, E. and Miller, W., CABIOS, 4:11-17, 1988). As an index for considering properties of amino acids at the time of the alignment, BLOSUM62 was used, which is commonly used as a matrix expressing the relationships of the same or different types of amino acids as numerical values. According to the alignment results, orthologs were classified into three ranks of those having identities of 95% or more, 60% or more and less than 95%, and less than 60%.

Because orthologs having an identity of 95% or more constitute a group of extremely conserved proteins primarily consisting of ribosomal proteins, differences in their thermostability are not expected. Furthermore, because orthologs having an identity of less than 60% include an increased number of amino acid substitutions, it becomes more unlikely that the objective amino acid substitutions can be extracted. Therefore, these orthologs were excluded.

On the other hand, when a value called p-distance (Nei M. et al., Molecular Evolution and Phylogenetics, pp. 17-31, Oxford University Press, New York, 2000) was calculated for orthologs having an identity of 60% or more and less than 95%, a result of 0.20 was obtained. It is thought that when this p-distance value is less than 0.3, it is unnecessary to consider the possibility that different mutations may occur at the same site, or a mutation may occur twice or more at the same site after differentiation of species. Because orthologs having an identity of less than 60% have a p-distance of 0.40, exclusion of orthologs having an identity less than 60% is considered appropriate. For the above reasons, 1430 orthologs having an identity of 60% or more and less than 95% were used for the analysis of amino acid substitutions.

The results of the alignment were compiled as a matrix of the numbers of the amino acid substitutions for all the amino acids on the assumption that amino acid substitutions are in one-to-one amino acid correspondence (Table 1). In Table 1, the amino acids of *Corynebacterium glutamicum* are shown in the vertical direction, and the amino acids of *Corynebacterium efficiens* are shown in the horizontal direction. For example, when a proline in *Corynebacterium efficiens* gene is substituted for an alanine residue in a gene sequence of *Corynebacterium glutamicum*, this substitution is entered in the cell at the intersection of the first row and the thirteenth column.

The aforementioned matrix was assumed as a mathematical matrix (hereinafter, referred to as "A"), and (matrix A—transposed matrix $A^{-1}$)/2 was calculated to evaluate amino acid substitutions of the reverse direction at the same time (hereinafter, this calculation result is referred to as "substitution evaluation index"). By this procedure, a certain substitution of the reverse direction (for example, mutation from arginine to lysine for mutation from lysine to arginine) can be converted into a single numerical value, and a value for an amino acid showing no substitution can be represented as zero. The calculation results obtained as described above were aligned in the descending order of the substitution evaluation index.

TABLE 1

Numbers of all amino acid substitutions in orthologs having homology of 60%

| A | C | D | E | F | G | H | I | K | L |
|---|---|---|---|---|---|---|---|---|---|
| 50566 | 96 | 648 | 1244 | 90 | 1316 | 146 | 259 | 283 | 463 |
| 73 | 3068 | 3 | 9 | 22 | 37 | 4 | 19 | 4 | 25 |
| 679 | 2 | 27982 | 3055 | 13 | 794 | 187 | 20 | 114 | 38 |
| 1428 | 3 | 3113 | 28520 | 9 | 560 | 170 | 53 | 348 | 103 |
| 135 | 20 | 18 | 15 | 17176 | 49 | 126 | 245 | 7 | 868 |
| 1265 | 28 | 581 | 314 | 28 | 43863 | 62 | 28 | 69 | 64 |
| 149 | 5 | 149 | 147 | 54 | 97 | 9466 | 23 | 72 | 78 |
| 385 | 15 | 35 | 66 | 187 | 56 | 38 | 24516 | 35 | 2191 |
| 578 | 8 | 284 | 593 | 11 | 248 | 157 | 54 | 12938 | 123 |
| 494 | 35 | 44 | 105 | 596 | 92 | 124 | 1642 | 72 | 48877 |
| 160 | 4 | 13 | 25 | 71 | 28 | 19 | 331 | 36 | 1170 |
| 396 | 13 | 1321 | 373 | 22 | 557 | 416 | 51 | 273 | 43 |
| 656 | 6 | 199 | 235 | 15 | 148 | 51 | 21 | 71 | 76 |
| 528 | 6 | 296 | 1121 | 20 | 248 | 342 | 42 | 415 | 190 |
| 301 | 26 | 113 | 195 | 23 | 238 | 295 | 37 | 664 | 173 |
| 3378 | 109 | 682 | 659 | 58 | 1013 | 173 | 81 | 215 | 139 |
| 1603 | 40 | 415 | 510 | 50 | 313 | 126 | 353 | 235 | 263 |
| 1485 | 48 | 101 | 265 | 174 | 129 | 50 | 3585 | 65 | 1529 |
| 27 | 8 | 3 | 4 | 67 | 29 | 17 | 6 | 0 | 58 |
| 43 | 16 | 20 | 16 | 650 | 22 | 307 | 22 | 9 | 63 |

| M | N | P | Q | R | S | T | V | W | Y |
|---|---|---|---|---|---|---|---|---|---|
| 134 | 241 | 1019 | 475 | 536 | 2372 | 1763 | 1634 | 28 | 37 |
| 7 | 4 | 5 | 6 | 34 | 86 | 38 | 55 | 0 | 12 |
| 13 | 747 | 237 | 283 | 140 | 447 | 427 | 91 | 2 | 24 |
| 42 | 255 | 406 | 1096 | 460 | 419 | 641 | 321 | 5 | 13 |
| 100 | 18 | 41 | 26 | 52 | 75 | 78 | 259 | 82 | 876 |
| 18 | 263 | 163 | 100 | 227 | 610 | 247 | 142 | 19 | 12 |
| 14 | 221 | 74 | 299 | 443 | 120 | 156 | 54 | 5 | 178 |
| 414 | 33 | 69 | 57 | 94 | 91 | 435 | 4332 | 18 | 31 |

TABLE 1-continued

Numbers of all amino acid substitutions in orthologs having homology of 60%

| 73    | 312   | 188   | 727   | 2855  | 320   | 600   | 136   | 14   | 16    |
|-------|-------|-------|-------|-------|-------|-------|-------|------|-------|
| 1095  | 39    | 167   | 219   | 306   | 126   | 356   | 1626  | 71   | 95    |
| 10591 | 15    | 30    | 57    | 58    | 32    | 153   | 410   | 15   | 15    |
| 28    | 12726 | 123   | 273   | 333   | 708   | 678   | 88    | 5    | 48    |
| 20    | 36    | 25111 | 122   | 156   | 297   | 254   | 121   | 5    | 15    |
| 74    | 192   | 240   | 13003 | 978   | 237   | 420   | 157   | 8    | 26    |
| 23    | 137   | 139   | 372   | 29928 | 229   | 322   | 92    | 27   | 32    |
| 67    | 623   | 623   | 353   | 525   | 23062 | 2623  | 264   | 22   | 48    |
| 182   | 386   | 395   | 313   | 423   | 1723  | 26670 | 897   | 12   | 27    |
| 366   | 52    | 197   | 136   | 182   | 177   | 994   | 38327 | 25   | 38    |
| 9     | 0     | 6     | 3     | 40    | 12    | 13    | 26    | 7589 | 32    |
| 13    | 30    | 16    | 21    | 47    | 38    | 31    | 49    | 58   | 11115 |

(5) Narrowing of the Amino Acid Substitutions Involved in Thermostability

Deviations of amino acid substitutions of orthologs belonging to the rank of identity of 60% or more and less than 95% were aligned in the descending order of the number of substitutions. The result is shown in Table 2. When they are described in the order of *Corynebacterium glutamicum-Corynebacterium efficiens*, substitutions of lysine-arginine, serine-alanine, serine-threonine, and isoleucine-valine were substitutions of the four highest substitution evaluation indices. Among these, it is known that isoleucine, valine, leucine and methionine are amino acids that are easily mutated from one to another (Kreil, D. P. et al., Nucleic Acids Res. 29: 1608-1615, 2001). From the above, the mutation patterns of the highest three substitution evaluation indices, which showed greater directivity than the mutation from isoleucine to valine, were predicted to be the amino acid substitutions involved in the higher thermostability of *Corynebacterium efficiens* in comparison with *Corynebacterium glutamicum*.

TABLE 2

Amino acid substitutions of the highest 10 substitution evaluation indices in orthologs having identity of 60 to 95%

| C. glutamicum | C. efficiens | Substitution evaluation index |
|---------------|--------------|-------------------------------|
| Lys           | Arg          | 1095.5                        |
| Ser           | Ala          | 503                           |
| Ser           | Thr          | 450                           |
| Ile           | Val          | 373.5                         |
| Gln           | Arg          | 303                           |
| Asn           | Asp          | 287                           |
| Ile           | Leu          | 274.5                         |
| Ser           | Gly          | 201.5                         |
| Lys           | Thr          | 182.5                         |
| Ala           | Pro          | 181.5                         |

EXAMPLE 3

Verification of Amino Acid Substitutions Involved in Thermostability by Comparison of Thermostability of Enzymes in *Corynebacterium glutamicum* and *Corynebacterium efficiens*

<1> Bacterial Strains Used

Mesophilic bacterium: *Corynebacterium glutamicum* ATCC 13869 strain

Thermophilic bacterium: *Corynebacterium efficiens* AJ1234 strain

<2> Media

[Glutamic Acid Production Medium]

80 g/l of glucose, 1 g/l of $KH_2PO_4$, 0.4 g/l of magnesium sulfate, 480 mg/l of soybean hydrolysate, 200 μg/l of vitamin B1-HCl, 300 μg/l biotin, pH 8.0. pH was adjusted with potassium hydroxide.

[Medium for Measurement of Isocitrate Lyase Activity]

4% of glucose or acetic acid, 5 g/l of ammonium sulfate, 5 g/l of urea, 0.5 g/l of $KH_2PO_4$, 0.5 g/l of $K_2HPO_4$, 20.9 μl of 3-[N-morpholino]propanesulfonic acid (MOPS), 0.25 g/l of magnesium sulfate heptahydrate, 10 mM of calcium chloride heptahydrate, 0.2 mg/l of copper sulfate heptahydrate, 0.2 mg/l of biotin, 10 mg/l of manganese sulfate heptahydrate, 10 mg/l of iron sulfate heptahydrate, 1 mg/l of zinc sulfate heptahydrate, pH 6.5. pH was adjusted with potassium hydroxide.

[CM2G Medium]

20 g/l of polypeptone, 20 g/l of yeast extract, 5 g/l of sodium chloride, 20 g/l of glucose, pH 7.0. pH was adjusted with sodium hydroxide.

All the media were sterilized at 120° C. for 20 minutes.

<3> Measurement of Enzymatic Activity

Measurement of Thermostability of Aspartate Kinase

Cells of each strain were cultured in the glutamic acid production medium, collected and then washed with 0.02 M $KH_2PO_4$ (pH 6.75)/0.03 M α-mercaptoethanol. Then, the cells were disrupted by ultrasonication and centrifuged at 33,000 rpm for 1 hour. Ammonium sulfate was added to the obtained supernatant to 80% saturation, and precipitates were obtained by centrifugation. The obtained precipitates were dissolved in 20 mM $KH_2PO_4$ (pH 6.75)/30 mM β-mercaptoethanol and used as a crude enzyme solution.

The crude enzyme solution was pretreated at 30 to 80° C. for 1, 3, 5 or 10 minutes and reacted with a reaction mixture at 30° C. The reaction mixture was prepared by adding the crude enzyme solution to an aqueous solution containing 100 mM Tris-HCl (pH 7.5), 10 mM ATP (pH 7.5), 600 mM hydroxylamine, 600 mM ammonium sulfate, 10 mM magnesium sulfate, 50 mM L-aspartic acid (pH 7.5), and adjusted to the total volume of 500 μl with sterilized water. The reaction was allowed to proceed for a predetermined period of time, and the reaction was terminated by addition of 750 μl of a reaction terminating solution. The reaction terminating solution had a composition of 4% trichloroacetic acid, 10% $FeCl_2$ and 1.4 N hydrochloric acid. The reaction mixture added with the reaction terminating solution was centrifuged at 15,000 rpm for 5 minutes, and the absorbance of the supernatant was measured at a wavelength of 540 nm. This measurement was performed for quantifying color development of hydroxymate produced by the reaction in which L-aspartic acid phosphoric acid salt, ADP and hydroxymate were produced from L-aspartic acid, ATP and hydroxylamine. The reaction mixture not containing L-aspartic acid was used as a blank.

(2) Measurement of Thermostability of Dihydrodipicolinate Synthase

Cells of each strain were cultured in the glutamic acid production medium, and cells in the logarithmic growth phase were collected and washed with 0.85% NaCl. The cell suspension was ultrasonicated and centrifuged at 60,000 rpm for 30 minutes, and the resultant supernatant was used as a crude enzyme solution.

The crude enzyme solution was pretreated beforehand at 60° C. for 1, 3, 5, 10 or 15 minutes and reacted with a reaction mixture at 37° C. The reaction mixture was prepared by adding the crude enzyme solution to 50 mM imidazole hydrochloride (pH 7.4), 2 mM aspartate β-semialdehyde (ASA) and 2 mM sodium pyruvate and adjusted to the total volume of 700 µl with sterilized water.

The activity was measured based on the increase in absorbance of the reaction mixture at 270 nm. For this measurement, the absorbance of dihydroxypicolinate non-enzymatically produced from a product of the reaction involving aspartate β-semialdehyde and pyruvic acid as substrates and catalyzed by dihydrodipicolinate synthase was measured. The reaction mixture not containing sodium pyruvate was used as a blank.

(3) Measurement of Thermostability of Diaminopimelate Dehydrogenase

Cells of each strain were cultured in the glutamic acid production medium, and cells in the logarithmic growth phase were collected, washed twice with 0.2% potassium chloride, and suspended in 40 mM potassium phosphate buffer (pH 7.5). The suspension was ultrasonicated and centrifuged at 15,000 rpm for 30 minutes. The resultant supernatant was used as a crude enzyme solution.

The crude enzyme solution was pretreated beforehand at 60° C. for 1, 3, 5, 10 or 15 minutes and reacted with a reaction mixture at 37° C. The reaction mixture was prepared by adding the crude enzyme solution to 200 mM glycine/potassium chloride buffer (pH 7.5, pH was adjusted with sodium hydroxide), 4 mM mesodiaminopimelic acid and 1 mM NADP, and adjusted to the total volume of 700 µl with sterilized water.

The activity was measured based on the increase in absorbance of the reaction mixture at 340 nm. For this measurement, the absorbance of NADPH produced by the reaction involving mesodiaminopimelic acid as a substrate and catalyzed by diaminopimelate dehydrogenase was measured, because the reaction requires $NADP^+$ as a coenzyme. The reaction mixture not containing mesodiaminopimelic acid was used as a blank.

(4) Measurement of Thermostability of Diaminopimelate Decarboxylase

Cells of each strain were cultured in the glutamic acid production medium, and the cells in the logarithmic growth phase were collected, washed twice with 50 mM potassium phosphate buffer (pH 7.0), suspended in 50 mM potassium phosphate buffer (pH 7.0) containing 6 mM mercaptoethanol, and disrupted by ultrasonication. The suspension was centrifuged at 15,000 rpm for 30 minutes, and the resultant supernatant was used as a crude enzyme solution.

The crude enzyme solution was pretreated beforehand at 30 to 80° C. for 1, 3, 5 or 10 minutes and reacted with a reaction mixture at 37° C. for 30 minutes. The reaction mixture was prepared by adding the crude enzyme solution to 20 mM diaminopimelic acid and 67 µM pyridoxal phosphate and adjusted to the total volume of 300 µl with sterilized water. Sulfuric acid was used to terminate the reaction, and potassium hydroxide was used for neutralization. The enzymatic activity was determined by measuring the amount of lysine produced by the reaction using Biotech Analyzer. The reaction mixture not containing mesodiaminopimelic acid was used as a blank.

(5) Measurement of Thermostability of Isocitrate Dehydrogenase

Cells of each strain were cultured in the glutamic acid production medium, washed three times with 50 mM Tris-HCl (pH 7.5), and disrupted by ultrasonication. The suspension was centrifuged at 15,000 rpm for 10 minutes, and the resultant supernatant was used as a crude enzyme solution. In a volume of 20 µl of the crude enzyme solution pretreated beforehand at 45° C. for 1, 3, 5, 10 or 15 minutes was reacted with 780 µl of a reaction mixture at 30° C. The reaction mixture contained 35 mM Tris-HCl/0.35 mM EDTA (pH 7.5), 1.5 mM manganese sulfate, 0.1 mM NADP and 1.3 mM sodium isocitrate. The activity was calculated by measuring the absorbance of NADPH produced by the reaction catalyzed by isocitrate dehydrogenase, because the reaction utilizes $NADP^+$ as a coenzyme.

(6) Measurement Of thermostability of Aconitase

Cells of each strain were cultured in the glutamic acid production medium, washed three times with 50 mM Tris-HCl (pH 7.5), and disrupted by ultrasonication. The suspension was centrifuged at 15,000 rpm for 10 minutes, and the obtained supernatant was used as a crude enzyme solution. In a volume of 20 µl, the crude enzyme solution was pretreated at 50° C. for 1, 3, 5 or 10 minutes, and then was reacted with 780 µl of a reaction mixture at 30° C. The reaction mixture contained 20 mM Tris-HCl (pH 7.5), 50 mM sodium chloride and 20 mM trisodium isocitrate. The activity was calculated by measuring the absorbance at 240 nm originated from cis-aconitate produced by the reaction.

(7) Measurement of Thermostability of Phosphoenolpyruvate Carboxylase

Cells of each strain were cultured in the glutamic acid production medium, washed three times with a washing buffer, and disrupted by ultrasonication. The suspension was centrifuged at 15,000 rpm for 10 minutes to remove disrupted cell debris. The washing buffer contained 100 mM Tris-HCl (pH 8.0), 10 mM magnesium sulfate, 1 mM dithiothreitol (DTT) and 20% glycerol. The supernatant was further centrifuged at 60,000 rpm for 1 hour, and the resultant supernatant was used as a crude enzyme solution.

In an amount of 20 µl, the crude enzyme solution was pretreated at 45° C. for 1, 3, 5, 10 or 20 minutes, and then was reacted with 780 µl of a reaction mixture at 20° C. The reaction mixture contained 100 mM Tris-$H_2SO_4$ (pH 8.5), 5 mM phosphoenolpyruvate, 10 mM $KHCO_3$, 0.1 mM acetyl-CoA, 0.15 mM NADH, 10 mM magnesium sulfate, 10 U of malate dehydrogenase and 0.1 mM dithiothreitol. The activity was calculated on the basis of decrease of NADH consumed by the reaction determined by measuring the absorbance at 340 nm for 2 minutes.

(8) Measurement of Thermostability of 2-Oxoglutarate Dehydrogenase

Cells of each strain were cultured in the glutamic acid production medium, washed twice with 0.2% potassium chloride, suspended in a solution containing 100 mM N-tris (hydroxymethyl)methyl-2-aminoethanesulfonic acid (TES)-NaOH (pH 7.5) and 30% glycerol, and disrupted by ultrasonication. The suspension was then centrifuged at 10000×g for 30 minutes to obtain a supernatant. The resultant supernatant was desalted by using Sephadex G-25, and the resultant solution was used as a crude enzyme solution.

The crude enzyme solution was pretreated beforehand at 50° C. for 1, 3, 5 or 10 minutes and reacted with a reaction mixture at 37° C. The reaction mixture contained 100 mM TES-NaOH (pH 7.7), 5 mM magnesium chloride, 0.2 mM coenzyme A (CoA), 0.3 mM thiamin pyrophosphate (TPP), 1 mM α-ketoglutaric acid, 3 mM L-cysteine and 1 mM acetylpyridine adenine dinucleotide (APDPN). The activity was calculated based on the decrease of APDPN, which is an analogue of NADP used as a coenzyme in the aforementioned reaction, and determined by measuring the absorbance at 365 nm (Usuda Y. et al., Microbiology, 142:3347-3354, 1996).

(9) Measurement of Thermostability of Isocitrate Lyase

Cells of each strain were cultured in the medium for measurement of isocitrate lyase activity, washed twice with 50 mM Tris-HCl (pH 7.3), and disrupted by ultrasonication. The suspension was centrifuged at 13,000×g for 30 minutes, and the resultant supernatant was used as a crude enzyme solution. The crude enzyme solution was pretreated at 50° C. for 5 minutes and then reacted with a reaction mixture at 37° C. The reaction mixture contained 50 mM MOPS-NaOH (pH 7.3), 5 mM DTT, 15 mM magnesium chloride, 1 mM EDTA, 5 mM dithiothreitol, 0.2 mM NADH and 18 U of lactate dehydrogenase (LDH). The activity was calculated on the basis of decrease of NADH consumed by the reaction determined by measuring the absorbance at 340 nm (Reinscheid, D. J. et al., J. Bacteriol., 176:3474-3483, 1994).

(10) Measurement of Thermostability of Phosphofructokinase

Cells of each strain were cultured in the CM2G medium, washed twice with 0.1 M Tris-HCl (pH 7.5), and disrupted by ultrasonication. Then, the suspension was centrifuged at 13,000×g for 30 minutes, and the resultant supernatant was used as a crude enzyme solution.

The crude enzyme solution was pretreated at 50° C. for 1, 3, 5 or 10 minutes, and then reacted with a reaction mixture at 37° C. The reaction mixture contained 100 mM Tris-HCl (pH 8.2), 0.2 mM NADH, 10 mM magnesium chloride, 2 mM ammonium chloride, 10 mM potassium chloride, 0.2 mM phosphoenolpyruvate, 6.4 mM fructose-6-phosphate, 1 mM ATP and 40 μg of lactate dehydrogenase/pyruvate kinase (LDH/PK). The activity was calculated based on the decrease of NADH consumed by the reaction determined by measuring the absorbance at 340 nm (Mori M. et al., Agric. Biol. Chem., 51:2671-2678, 1987; Campos G et al., J. Biol. Chem., 259:6147-6152, 1984).

(11) Measurement of Thermostability of Fructose-1-phosphate Kinase

Cells of each strain were cultured in the CM2G medium, washed twice with 0.1 M Tris-HCl (pH 7.5), and disrupted by ultrasonication. Then, the suspension was centrifuged at 13,000×g for 30 minutes, and the resultant supernatant was used as a crude enzyme solution.

The crude enzyme solution was pretreated at 50° C. for 1,3, 5 or 10 minutes, and then reacted with a reaction mixture at 37° C. The reaction mixture contained 100 mM Tris-HCl (pH 8.2), 0.2 mM NADH, 10 mM magnesium chloride, 2 mM ammonium chloride, 10 mM potassium chloride, 0.2 mM phosphoenolpyruvate, 6.4 mM fructose-1-phosphate, 1 mM ATP and 40 μg of lactate dehydrogenase/pyruvate kinase. The activity was calculated based on the decrease of NADH consumed by the reaction determined by measuring the absorbance at 340 nm.

(12) Measurement of the Thermostability of Citrate Synthase

Cells of each strain were cultured in the glutamic acid production medium, washed three times with 0.2 M sodium glutamate hydrate and 50 mM Tris-HCl (pH 7.5), and disrupted by ultrasonication. The suspension was centrifuged at 10,000 rpm for 10 minutes, and the resultant supernatant was used as a crude enzyme solution.

The crude enzyme solution was pretreated at 50° C. for 5 minutes, and then reacted with a reaction mixture at 30° C. The reaction mixture contained 0.1 M sodium glutamate hydrate, 0.1 mM 5,5'-dithiobis-(2-nitrobenzoic acid) (DTNB), 0.3 mM acetyl-CoA and 0.5 mM oxaloacetic acid. The activity was calculated by measuring the increase of the absorbance at 412 nm of thiol-CoA (HS-CoA) mercaptide produced by the reaction (Srera, P. A., Method in Enzymol., 13:11-26, 1969; Eikmanns B. J. et al., Microbiology, 140: 1817-1828, 1994).

<4> Verification of Correlations between Amino Acid Substitutions and Thermostability of Enzymes For each enzyme, the number of three types of amino acid substitutions predicted in Example 2 as amino acid substitutions involved in thermostability of *Corynebacterium efficiens* (Lys→Arg, Ser→Ala and Ser→Thr, these directions are defined as positive directions) and the number of substitutions in the reverse directions of these amino acid substitutions (Arg→Lys, Ala→Ser and Thr→Ser, these directions are defined as negative directions) were counted. Then, the number of each substitution in the negative direction was subtracted from the number of the substitution in the positive direction to express the extents of the amino acid substitutions with numerical values (hereinafter, each obtained numerical value is referred to as "point"). Subsequently, for each enzyme, data about which enzyme derived from *Corynebacterium glutamicum* or enzyme derived from *Corynebacterium efficiens* showed higher thermostability was compared with the point. The results are shown in Table 3.

Among the enzymes shown in Table 3, the gene sequences of *Corynebacterium efficiens* encoding 2-oxoglutarate dehydrogenase, isocitrate lyase, phosphofructokinase, fructose-1-phosphate kinase (phosphofructokinase), isocitrate dehydrogenase, aconitase, phosphoenolpyruvate carboxylase and citrate synthase and the amino acid sequences encoded thereby are disclosed in WO01/25447. Furthermore, the gene sequences of *Corynebacterium efficiens* encoding aspartate kinase, dihydrodipicolinate synthase, diaminopimelate dehydrogenase and diaminopimelate decarboxylase and the amino acid sequences encoded thereby are disclosed in Japanese Patent Laid-open Publication (Kokai) No. 2001-120270.

TABLE 3

Results of comparison of experimental data about enzyme thermostability with points

| Number | Enzyme | Species showing higher thermostability | Point | Prediction results |
|---|---|---|---|---|
| 1 | 2-Oxoglutarate dehydrogenase | C. efficiens | 0 | Δ |
| 2 | Isocitrate lyase | C. efficiens | 2 | ○ |
| 3 | Phosphofructokinase | C. efficiens | −3 | X |
| 4 | Fructose-1-phosphate kinase | C. efficiens | 5 | ○ |
| 5 | Isocitrate dehydrogenase | C. efficiens | 4 | ○ |
| 6 | Aconitase | C. efficiens | 0 | Δ |
| 7 | Phosphoenolpyruvate carboxylase | C. efficiens | 10 | ○ |

TABLE 3-continued

Results of comparison of experimental data about enzyme thermostability with points

| Number | Enzyme | Species showing higher thermostability | Point | Prediction results |
|---|---|---|---|---|
| 8 | Citrate synthase | C. efficiens | 3 | ○ |
| 9 | Aspartate kinase | C. glutamicum | −1 | ○ |
| 10 | Dihydrodipicolinate synthase | C. efficiens | 0 | Δ |
| 11 | Diaminopimelate dehydrogenase | C. glutamicum | −2 | ○ |
| 12 | Diaminopimelate decarboxylase | C. efficiens | 2 | ○ |

If the point is positive, the enzyme derived from *Corynebacterium efficiens* was expected to be more thermostable, whereas if the point was negative, the enzyme derived from *Corynebacterium glutamicum* was expected to be more thermostable.

As for 2-oxoglutarate dehydrogenase, the enzyme derived from *Corynebacterium efficiens* was more thermostable. However, the point was 0, and thus prediction based on the point was impossible (denoted with Δ in Table 2).

As for isocitrate lyase, the enzyme derived from *Corynebacterium efficiens* was more thermostabilized, and the point was 2, that is, positive. Thus, the experimental result matched the prediction (denoted with ○ in Table 2).

As for phosphofructokinase, the enzyme derived from *Corynebacterium efficiens* was more thermostabilized. However, the point was negative, and thus the experimental result did not match the prediction (denoted with X in Table 2).

As for fructose-1-phophate kinase, the enzyme derived from *Corynebacterium efficiens* was more thermostabilized, and the point was 5, that is, positive. Thus, the experimental result matched the prediction.

As for isocitrate dehydrogenase, the enzyme derived from *Corynebacterium efficiens* was more thermostabilized, and the point was 4, that is, positive. Thus, the experimental result matched the prediction.

As for aconitase, the enzyme derived from *Corynebacterium efficiens* was more thermostabilized. However, the point was 0, and prediction based on the point was impossible.

As for phosphoenolpyruvate carboxylase, the enzyme derived from *Corynebacterium efficiens* was more thermostabilized, and the point was 10, that is, positive. Thus, the experimental result matched the prediction.

As for citrate synthase, the enzyme derived from *Corynebacterium efficiens* was more thermostabilized, and the point was 3, that is, positive. Thus, the experimental result matched the prediction.

As for aspartate kinase, the enzyme derived from *Corynebacterium glutamicum* was more thermostabilized, and the point was −1, that is, negative. Thus, the experimental result matched the prediction.

As for dihydrodipicolinate synthase, the enzyme derived from *Corynebacterium efficiens* was more thermostabilized. However, the point was 0, and thus prediction based on the point was impossible.

As for diaminopimelate dehydrogenase, the enzyme derived from *Corynebacterium glutamicum* was more thermostabilized, and the point was −2, that is, negative. Thus, the experimental result matched the prediction.

As for diaminopimelate decarboxylase, the enzyme derived from *Corynebacterium efficiens* was more thermostabilized, and the point was 2, that is, positive. Thus, the experimental result matched the prediction.

As described above, the directivity of thermostabilization could be correctly predicted for 8 enzymes in 12 enzymes of which enzymatic activities were measured, and could not be predicted for 3 enzymes, whereas the experimental result did not match the point only in one enzyme. Prediction with such a high probability was possible by considering directions of only 3 amino acid substitutions.

Industrial Applicability

According to the present invention, a property of a protein such as thermostability can be modified by using only information on the primary structure without using information on the secondary structure and tertiary structure of the protein. In particular, thermostability of proteins produced by mesophilic bacteria or mesophilic bacteria themselves currently being industrially used can be improved.

While the invention has been described with reference to preferred embodiments thereof, it will be apparent to one skilled in the art that various changes can be made, and equivalents employed, without departing from the scope of the invention. All the cited references herein, including the foreign priority document, JP 2002-57863, are incorporated as a part of this application by reference in its entirety.

We claim:

1. A method for modifying the thermostability of a protein, comprising
   (a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under an optimum growth condition wherein the optimum growth condition is the optimum growth temperature when compared with the first microorganism, and
   (b) comparing an amino acid sequence encoded by one of the said 1000 or more genes from the first microorganism to an amino acid sequence encoded by the orthologous gene from the second microorganism,
   (c) detecting substitutions between the amino acid sequence encoded by one of the said 1000 or more genes from the first microorganism and the amino acid sequence encoded by the orthologous gene from the second microorganism for each pair of orthologous genes,
   (d) compiling the detected amino acid substitutions for each amino acid substitution type,
   (e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism,
   (f) identifying and labelling the amino acid substitutions which occur at a high frequency, and
   (g) modifying the thermostability of said protein by introducing one or more mutations into a gene encoding said protein so that the amino acid substitutions identified in (f) occur.

2. The method according to claim 1, wherein genes having an identity of 60% or more and less than 95% on the amino acid sequence level are selected as genes which are orthologs to each other.

3. The method according claim 1, wherein the first microorganism and the second microorganism are coryneform bacteria.

4. The method according to claim 3, wherein the first microorganism is *Corynebacterium glutamicum*, and the second microorganism is *Corynebacterium efficiens*.

5. A method for producing a protein having a modified property comprising:
(a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under at least one optimum growth condition when compared with the first microorganism,
(b) comparing an amino acid sequence encoded by a gene from the first microorganism to an amino acid sequence encoded by the orthologous gene from the second microorganism,
(c) detecting substitutions between the amino acid sequence encoded by a gene from the first microorganism and the amino acid sequence encoded by a gene from the second microorganism for each pair of orthologous genes,
(d) compiling the detected amino acid substitutions for each amino acid substitution type,
(e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism,
(f) identifying and labelling the amino acid substitutions which occur at a high frequency as amino acid substitutions which are involved in said optimum growth condition, and
(g) introducing one or more of the amino acid substitutions identified in (f) into the gene encoding the protein to modify a property of the protein,
(h) introducing said gene obtained in (g) into a suitable host for gene expression to express the protein having a modified property.

6. The method according to claim 5, further comprising the steps of:
(i) testing the property of the protein obtained in (h), and
(j) selecting a protein having an improved property relating to said optimum growth condition.

7. The method according to claim 5, wherein said optimum growth condition is optimum growth temperature, and the property of the protein is thermostability.

8. A method for producing a microorganism having a modified property comprising:
(a) selecting 1000 or more genes from the genome of a first microorganism, and selecting 1000 or more genes from the genome of a second microorganism, wherein the genes from the first microorganism are orthologs to the genes from the second microorganism, and wherein the second microorganism is closely related to the first microorganism, but grows differently under at least one optimum growth condition when compared with the first microorganism,
(b) comparing an amino acid sequence encoded by a gene from the first microorganism to an amino acid sequence encoded by the orthologous gene from the second microorganism,
(c) detecting substitutions between the amino acid sequence encoded by a gene from the first microorganism and the amino acid sequence encoded by a gene from the second microorganism for each pair of orthologous genes,
(d) compiling the detected amino acid substitutions for each amino acid substitution type,
(e) calculating the frequency of each amino acid substitution type, wherein for each detected amino acid substitution type, a correction is made by subtracting the total number of substitution types which occur from the first microorganism to the second microorganism from the total number of the same substitution type which occurs in the reverse direction, or from the second microorganism to the first microorganism,
(f) identifying and labelling the amino acid substitutions which occur at a high frequency as amino acid substitutions which are involved in said optimum growth condition, and
(g) introducing one or more of the amino acid substitutions identified in (f) into a chromosomal DNA of a microorganism to modify a property of said microorganism.

9. The method according to claim 8, wherein said optimum growth condition is optimum growth temperature, and the property of the protein is thermostability.

* * * * *

UNITED STATES PATENT AND TRADEMARK OFFICE
CERTIFICATE OF CORRECTION

PATENT NO. : 8,510,053 B2
APPLICATION NO. : 10/933280
DATED : August 13, 2013
INVENTOR(S) : Yosuke Nishio et al.

It is certified that error appears in the above-identified patent and that said Letters Patent is hereby corrected as shown below:

On the Title Page
The second Assignee as indicated on the issue fee transmittal should be included as indicated below:

(73) Ajinomoto Co., Inc., Tokyo (JP)
National Institute of Technology and Evaluation, Tokyo (JP)

Signed and Sealed this
Fourth Day of February, 2014

Michelle K. Lee
*Deputy Director of the United States Patent and Trademark Office*